United States Patent
Dai et al.

(10) Patent No.: US 7,459,312 B2
(45) Date of Patent: Dec. 2, 2008

(54) PHOTODESORPTION IN CARBON NANOTUBES

(75) Inventors: Hongjie Dai, Sunnyvale, CA (US); Robert J. Chen, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 918 days.

(21) Appl. No.: 10/475,022

(22) PCT Filed: Apr. 18, 2002

(86) PCT No.: PCT/US02/12033

§ 371 (c)(1), (2), (4) Date: Mar. 29, 2004

(87) PCT Pub. No.: WO02/086480

PCT Pub. Date: Oct. 31, 2002

(65) Prior Publication Data

US 2004/0147037 A1      Jul. 29, 2004

Related U.S. Application Data

(60) Provisional application No. 60/284,846, filed on Apr. 18, 2001.

(51) Int. Cl.
*G01N 27/04* (2006.01)
*G01N 27/27* (2006.01)
*G01N 33/00* (2006.01)

(52) U.S. Cl. .............. 436/151; 422/82.01; 422/82.02; 422/88; 422/90; 422/98; 436/127; 436/136; 436/139; 436/140; 436/141; 436/142; 436/144; 436/149; 436/181; 436/183

(58) Field of Classification Search ... 422/82.01–82.02, 422/83, 88, 90, 98; 436/127, 136, 139–142, 436/144, 149, 151, 181, 183

See application file for complete search history.

(56) References Cited

U.S. PATENT DOCUMENTS

| | | | |
|---|---|---|---|
| 4,495,793 | A | 1/1985 | Hager |
| 5,436,167 | A | 7/1995 | Robillard |
| 5,448,906 | A | 9/1995 | Cheung |
| 5,626,650 | A | 5/1997 | Rodriguez et al. |
| 5,653,951 | A | 8/1997 | Rodriguez et al. |
| 5,866,434 | A | 2/1999 | Massey et al. |
| 6,159,742 | A | 12/2000 | Lieber et al. |
| 6,162,926 | A | 12/2000 | Murphy et al. |
| 7,129,554 | B2 | 10/2006 | Lieber et al. |

FOREIGN PATENT DOCUMENTS

JP     2000-61241     *   2/2000

OTHER PUBLICATIONS

Pchelarov, G. et al, Carbon 1997, 35, 755-758.*

(Continued)

*Primary Examiner*—Arlen Soderquist
(74) *Attorney, Agent, or Firm*—Crawford Maunu PLLC

(57) ABSTRACT

Carbon nanotube devices are manipulated in a manner that is useful for a variety of implementations. According to an example embodiment of the present invention, light (632) is used to photodesorb molecules from a carbon nanotube (620).

28 Claims, 4 Drawing Sheets

OTHER PUBLICATIONS

Lin, M. F. et al, Physical Review B 1997, 56, 1430-1439.*
Lin, M. F. et al, Physical Review B 1997, 56, 4996-5002.*
Tans, S. J. et al, Nature 1998, 393, 49-52.*
Sugano, M. et al, Chemical Physics Letters 1998, 292, 575-579.*
Pimenta, M. A. et al, Journal of Materials Research 1998, 13, 2396-2404.*
Martel, R. et al, Applied Physics Letters 1998, 73, 2447-2449.*
Chen, P. et al, Physical Review Letters 1999, 82, 2548-2551.*
Margulis, VI. A. et al, Physics Letters A 1999, 258, 394-400.*
Kataura, H. et al, Synthetic Metals 1999, 103, 2555-2558.*
Chen, P. et al, IUBMB Life 2000, 49, 105-108.*
Akira Koshio et al. "In Situ Laser-Furnance TOF Mass spectrometry of $C_{36}$ and the Large-Scale Production by Arc-Discharge." J. Phys. Chem. B. vol. 104, pp. 7908-7913 (Jul. 21, 2000).
Robert J. Chen, Hongjie Dai et al. "Molecular photodesportion from single-walled carbon nanotubes." Applied Physics Letters, vol. 79, No. 14, pp. 2258-2260 (Oct. 1, 2001).

* cited by examiner

PHOTODESORPTION IN CARBON NANOTUBES

RELATED PATENT DOCUMENTS

This patent application is the national stage filing under 35 U.S.C. § 371 of International Application No. PCT/US2002/012033 filed on Apr. 18, 2002; which claims benefit under 35 U.S.C. § 119(e) of U.S. Provisional Application Ser. No. 60/284,846 filed on Apr. 18, 2001, both of which are incorporated herein by reference.

This patent document also relates to application Ser. No. 09/574,393 (now U.S. Pat. No. 6,528,020), filed on May 19, 2000 and entitled "Carbon Nanotube Devices," which is a divisional/continuation-in-part of application Ser. No. 09/133,948 (now U.S. Pat. No. 6,346,189), filed on Aug. 14, 1998 and entitled "Carbon Nanotube Structures Made Using Catalyst Islands," and which claims priority to U.S. Provisional Application Ser. No. 60/171,200, filed on Dec. 15, 1999; and to U.S. Provisional Patent Application Ser. No. 60/335,306, entitled "Integrated Nanotubes for Electronic Noses" and filed on Nov. 1, 2001, all of which are fully incorporated herein by reference.

FEDERALLY SPONSORED RESEARCH OR DEVELOPMENT

This invention was supported in part by grant number ECS 9871947 from the National Science Foundation (NSF). The U.S. Government has certain rights in the invention.

FIELD OF THE INVENTION

The present invention relates generally to carbon nanotubes and more particularly to photo-induced desorption in carbon nanotubes and related applications.

BACKGROUND

Carbon nanotubes are unique carbon-based, molecular structures that exhibit interesting and useful electrical properties. There are two general types of carbon nanotubes, referred to as multi-walled carbon nanotubes (MWNTs) and single-walled carbon nanotubes (SWNTs). SWNTs have a cylindrical sheet-like, one-atom-thick shell of hexagonally-arranged carbon atoms, and MWNTs are typically composed of multiple coaxial cylinders of ever-increasing diameter about a common axis. Thus, SWNTs can be considered to be the structure underlying MWNTs and also carbon nanotube ropes, which are uniquely-arranged arrays of SWNTs.

Due to their unique electrical properties, carbon nanotubes are being studied for development in a variety of applications. These applications include, among others, chemical and bio-type sensing, field-emission sources, selective-molecule grabbing, nano-electronic devices, and a variety of composite materials with enhanced mechanical and electromechanical properties. More specifically, for example, in connection with chemical and biological detection, carbon nanotubes are being studied for applications including medical devices, environmental monitoring, medical/clinical diagnosis and biotechnology for gene mapping and drug discovery. For general information regarding carbon nanotubes, and for specific information regarding SWNTs and its applications, reference may be made generally to the above-mentioned patent documents, and also to: "Carbon Nanotubes: Synthesis, Structure, Properties and Applications," M. S. Dresselhaus, G. Dresselhaus and Ph. Avouris (Eds.), Springer-Verlag Berlin Heidelberg, New York, 2001; and "T. Single-shell Carbon Nanotubes of 1-nm Diameter," Iijima, S. & Ichihashi, Nature 363, 603-605 (1993).

In these and other carbon nanotube implementations, nanotube devices exhibiting both high functionality and high flexibility are desirable. For instance, in electrical applications, the ability to change electrical characteristics of a device to target the device's electrical behavior to a particular implementation increases the device's functionality and flexibility. Similarly, in chemical sensors, sensing a variety of molecular species using the same sensor or sensor arrangement is advantageous in applications where it is not feasible to use many different sensors (e.g., due to space, cost, response speed or other limitations). In previous carbon nanotube implementations, however, achieving high functionality and flexibility has been challenging. In particular, it has been difficult to readily remove molecules from carbon nanotubes for manipulating properties thereof.

SUMMARY

The present invention is directed to overcoming the above-mentioned challenges and others related to carbon nanotube devices and their implementations. The present invention is exemplified in a number of implementations and applications, some of which are summarized below.

According to an example embodiment of the present invention, light is directed to a carbon nanotube for desorbing molecules therefrom. In connection with this example embodiment, it has been discovered that light of a selected wavelength and intensity can be used to rapidly desorb molecules from a carbon nanotube. This rapid photodesorption has been found to be particularly applicable to molecular sensors, nanotube-based molecular electronics and optoelectronic devices.

In another example embodiment of the present invention, a molecular sensor includes a carbon nanotube and a light source adapted to direct light to the carbon nanotube for desorbing molecules therefrom. In this example embodiment, the light applied to the carbon nanotube cleans (desorbs) molecules from the carbon nanotube, such that the carbon nanotube can subsequently be used for detecting further molecules via adsorption. The subsequently adsorbed molecules are detected as a function of an electrical characteristic of the carbon nanotube, such as conductance, that changes in response to the adsorbed molecules. This approach is particularly useful for rapid recovery with such molecular sensors.

In another example embodiment of the present invention, a circuit arrangement includes a carbon nanotube having undergone photodesorption. In connection with this example embodiment, it has been discovered that carbon nanotubes having undergone photodesorption exhibit ambipolar characteristics. By applying a gating voltage to the carbon nanotube, p-type, n-type and insulative behavior can each be selectively elicited from the carbon nanotube, providing a flexible circuit.

In still another example embodiment of the present invention, a circuit arrangement includes a plurality of carbon nanotube devices, each of the carbon nanotube devices having a selectively programmed carbon nanotube. The selective programming is achieved via photodesorption of molecules from one or more of the carbon nanotubes, with the presence and absence of molecules adsorbed to the carbon nanotube being indicative of two distinct electrical states (e.g. two conductance states and/or "ON" and "OFF" states).

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
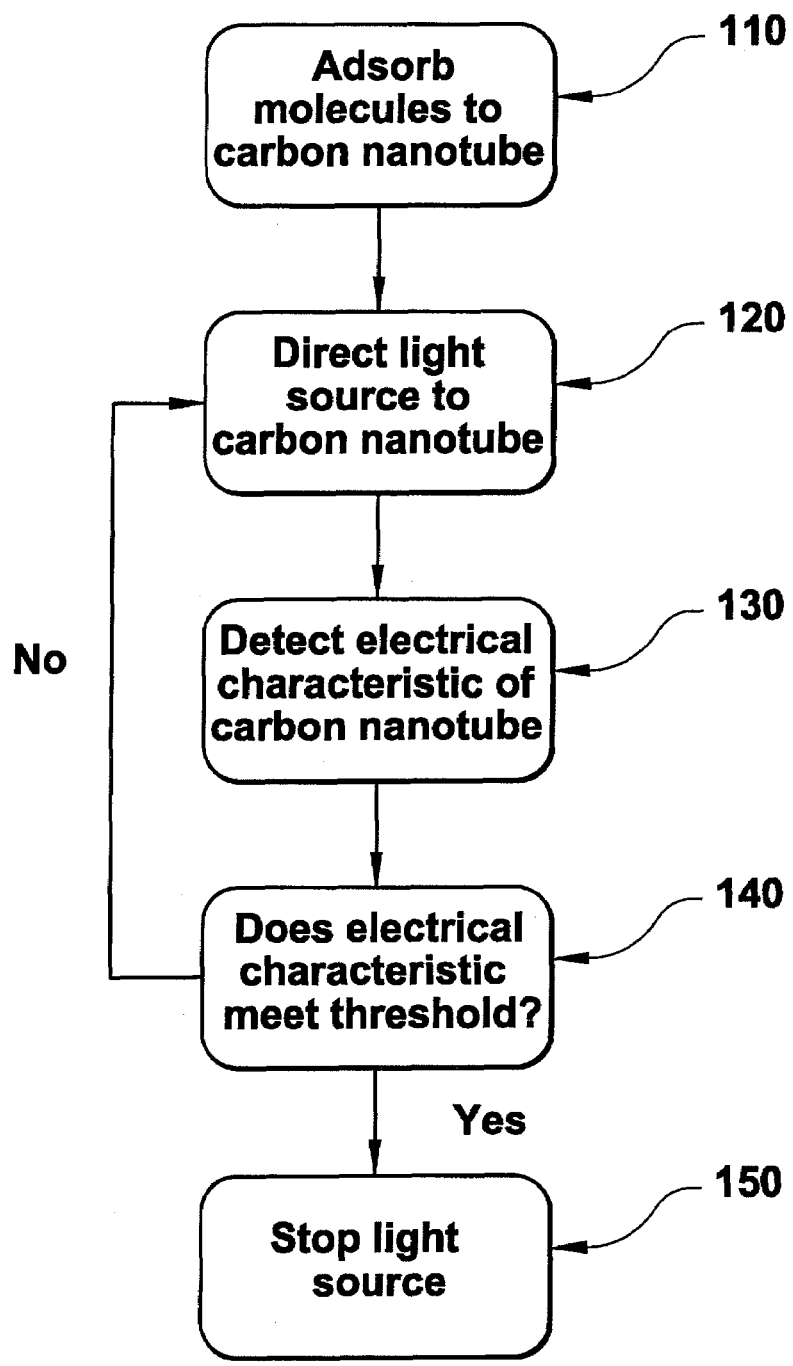
FIG. 1 is a flow diagram for molecular photodesorption from a carbon nanotube, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of different types of devices, and the invention has been found to be particularly suited for photo-induced desorption with carbon nanotubes. While the present invention is not necessarily limited to such applications, various aspects of the invention may be appreciated through a discussion of various examples using this context.

According to an example embodiment of the present invention, it has been discovered that light directed to a carbon nanotube induces molecular desorbtion therefrom, which in turn affects electrical and chemical properties of the carbon nanotube. This photo-induced desorption (photodesorption) is useful for removing undesirable molecules from the carbon nanotube, is highly efficient and desorbs molecules including both nearly chemisorbed and physisorbed molecules. For instance, when using the carbon nanotube to detect and/or isolate molecules via adsorption, it is useful to rapidly desorb molecules from the carbon nanotube prior to detecting and/or isolating additional molecules. In addition, when using the carbon nanotube in an electric circuit, it is useful to desorb molecules for manipulating one or more electrical characteristics of the carbon nanotube. With this approach, carbon nanotubes can be used to form molecular-scale wires that can be used in a variety of implementations, such as electronic circuits, molecular sensors and optoelectronic devices.

FIG. 1 is a flow diagram for photodesorption from a carbon nanotube, such as a SWNT, according to another example embodiment of the present invention. At block 110, molecules are adsorbed to the carbon nanotube. This adsorption may occur, for instance, unintentionally (e.g., when the carbon nanotube is exposed to air) or selectively by introducing a gas to the carbon nanotube, for example, via a gas inlet to a chamber. In the context of such selective adsorption, e.g., the carbon nanotube is exposed to a gas selected for manipulating one or more properties of the carbon nanotube via adsorption of molecules in the gas. This selective adsorption approach is particularly useful, for example, for adsorbing molecules for selectively setting an electrical characteristic of the nanotube, such as the resistance of the nanotube, for use in a microelectronic circuit. In another example, this selective adsorption approach is useful for making the carbon nanotube selective for further adsorption of a second type of molecule for detecting the presence thereof.

At block 120 of FIG. 1, a light source is used to direct light to the carbon nanotube and to desorb molecules therefrom. An electrical characteristic of the carbon nanotube is detected at block 130 and used as an indication of the quantity and/or composition of the adsorbed molecules. If the detected electrical characteristic meets a threshold at block 140, a sufficient amount of the molecules have been desorbed and the light source is stopped at block 150. If the threshold is not met at block 140, light is again directed at block 120 and the electrical characteristic detected at block 130 until the threshold is met.

The threshold used at block 140 is selected to correspond to one or more of a variety of electrical characteristics, depending upon the particular application in which the carbon nanotube is to be used. For example, when completely (or nearly completely) desorbing molecules from the carbon nanotube to remove a molecular species, the threshold is selected to be indicative of the carbon nanotube being free of the adsorbed molecules (e.g., the threshold corresponds to the behavior of the carbon nanotube prior to any adsorption). In another example, when a particular electrical characteristic (e.g., conductance) is desired for implementation of the carbon nanotube, the threshold is selected to correspond to the carbon nanotube exhibiting the desired characteristic.

In another example embodiment of the present invention, characteristics such as wavelength and intensity of light directed to the carbon nanotube at block 120 are selected to achieve one or more particular photodesorption characteristics. In connection with this example embodiment, it has been discovered that the photodesorption of molecules is dependent upon the wavelength of the light. For instance, it has been found that ultraviolet light having a wavelength of about 254 nanometers is useful for desorbing Oxygen from a carbon nanotube. As the wavelength of light varies from 254 nanometers, the desorbtion of Oxygen also varies (e.g., the rate of desorption of Oxygen may decrease or even approach zero). Also in connection with this example embodiment, it has been discovered that the intensity of the light similarly affects the photodesorption of the molecules, as discussed in connection with FIG. 4 below. In this regard, photodesorption characteristics, such as a particular rate of desorption, can be controlled by using light of different wavelengths and/or intensities. This approach is particularly useful for controlling the rate of change of characteristics of the carbon nanotube, such as the conductance of the carbon nanotube, or for optimizing the wavelength and intensity of light applied to the carbon nanotube for rapid desorption of molecules therefrom, as discussed in connection with FIGS. 2 and 3 below.

In another implementation, the wavelength of light directed to the carbon nanotube at block 120 is selected to correspond to the diameter of the carbon nanotube. In connection with this implementation, it has been discovered that photodesorption characteristics for carbon nanotubes vary in relation to the diameter of the carbon nanotube. Therefore, the diameter of the carbon nanotube undergoing photodesorption is used to select the wavelength of light applied at block 120. With this approach, it has been discovered that light having a wavelength of about 254 nanometers is particularly useful for photodesorption of molecules from a carbon nanotube having a diameter of about 1.5 nanometers.

In another particular example embodiment of the present invention, the light directed at block 120 causes $\pi$-electron plasmon excitation in the carbon nanotube (e.g., the collective excitation of $\pi$-electron oscillations in the nanotube), and the plasmon excitation induces molecular desorption from the carbon nanotube. More specifically, high electric fields associated with plasmon excitation enhance hot electron generation in the carbon nanotube, and collective electron oscillations in the carbon nanotube de-excite into single-particle hot electron excitations. The hot electrons attach to molecules adsorbed to the carbon nanotube and induce desorption therefrom. Part of the plasmon excitation energy is dissipated through breaking molecule-carbon nanotube binding.

Figure 2:
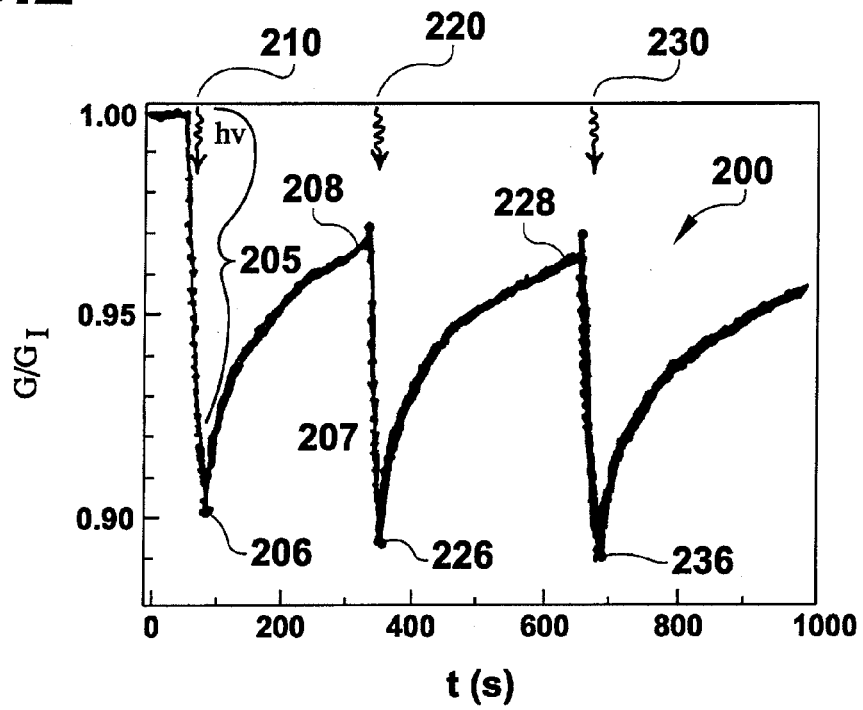
FIG. 2 is a graph showing normalized conductance over time of a carbon nanotube undergoing photodesorption, according to another example embodiment of the present invention.

In another example embodiment of the present invention, FIG. 2 shows conductance (G, being normalized by $G_I=(2.8 \text{ k}\Omega)^{-1}$) versus time (t) in seconds of a SWNT grown using CVD on a catalytically patterned $SiO_2$/Si substrate and controlled contacting with electron-beam lithography. Ultra-violet (UV) light having a wavelength of about 254 nanometers, an intensity of about 2 $mW/cm^2$ and a photon flux of about $2.5 \times 10^{15}/cm^2 s$ is directed at the SWNT at ambient conditions during time intervals 210, 220 and 230. The light desorbs molecules (e.g. Oxygen) from the SWNT and thereby lowers the SWNT's conductance. The photodesorption causes a reduction of hole-carriers in the SWNT and thus lowers its conductance.

Referring specifically to portion 205 of curve 200, the conductance of the SWNT decreases upon illumination with the ultraviolet light. Interval 210 corresponds to the curve portion 205, with the SWNT being illuminated with the UV light for about 25 seconds. At node 206, the UV illumination is ceased and the conductance of the SWNT recovers (increases) at a rate slower than the rate of decrease, shown by curve portion 207, due to the gradual re-adsorption of molecules (e.g., Oxygen from ambient air). With the re-application of UV light at node 208 for interval 220, the conductance again decreases to node 226 at a level slightly below the level at node 206, due to the light being applied at an initial conductance lower than that for interval 210. As the UV illumination of interval 220 is ceased, the conductance similarly recovers, and the cycle of conductance decrease followed by recovery is again repeated with interval 220. The approach shown in FIG. 2 may be useful, for example, for detecting the presence of molecules by adsorption to the carbon nanotube and subsequently cleaning the molecules from the carbon nanotube at the UV illumination intervals 210, 220 and 230.

Figure 3:
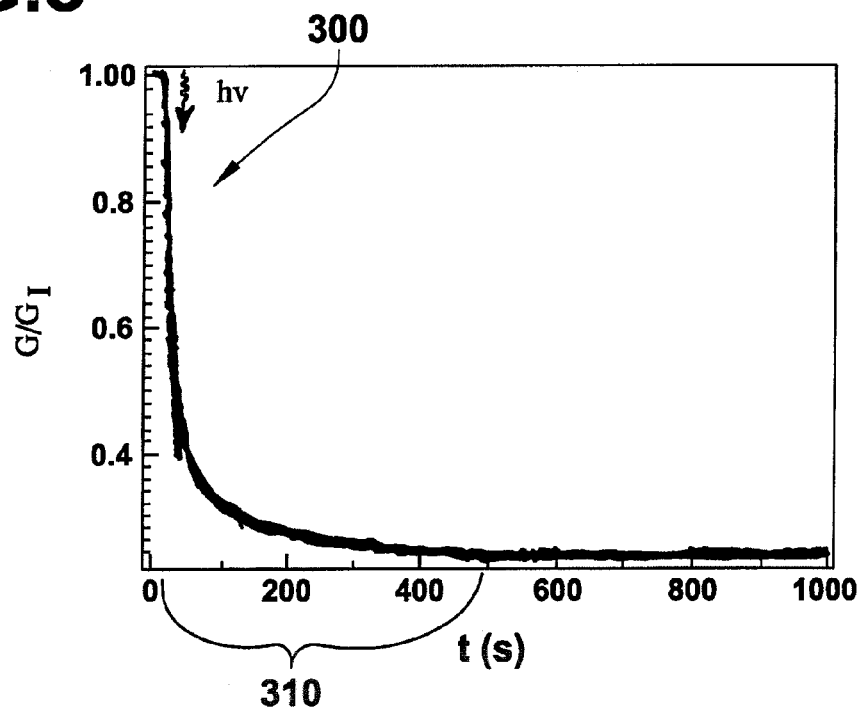
FIG. 3 is a graph showing conductance over time of a carbon nanotube undergoing photodesorption with ultraviolet (UV) light in a vacuum, according to another example embodiment of the present invention.

FIG. 3 shows conductance (G, normalized as in FIG. 2) versus time (t) in seconds of a SWNT undergoing photodesorption in a vacuum, according to another example embodiment of the present invention. A vacuum of about $1 \times 10^{-8}$ Torr is drawn on the SWNT, for example, using a vacuum chamber, and UV light having a wavelength of about 254 nanometers is directed at the SWNT for a time interval 310 of about 500 seconds. The light causes molecular photodesorption from the SWNT, and the molecules are removed from the SWNT via the vacuum. In one particular implementation, inert gas is introduced to the SWNT during the photodesorption. The normalized conductance of the SWNT, shown with curve 300, continually approaches zero throughout the time interval 310, with no appreciable recovery after removal of the light. With this approach, molecules such as Oxygen are readily removed from the SWNT. After the photodesorption, the SWNT can be subsequently implemented in a variety of circuit arrangements (e.g., by desorbing the molecules from the SWNT, the influence of the molecules upon certain electrical characteristics of the SWNT, such as the conductance of the SWNT, is removed).

Figure 4:
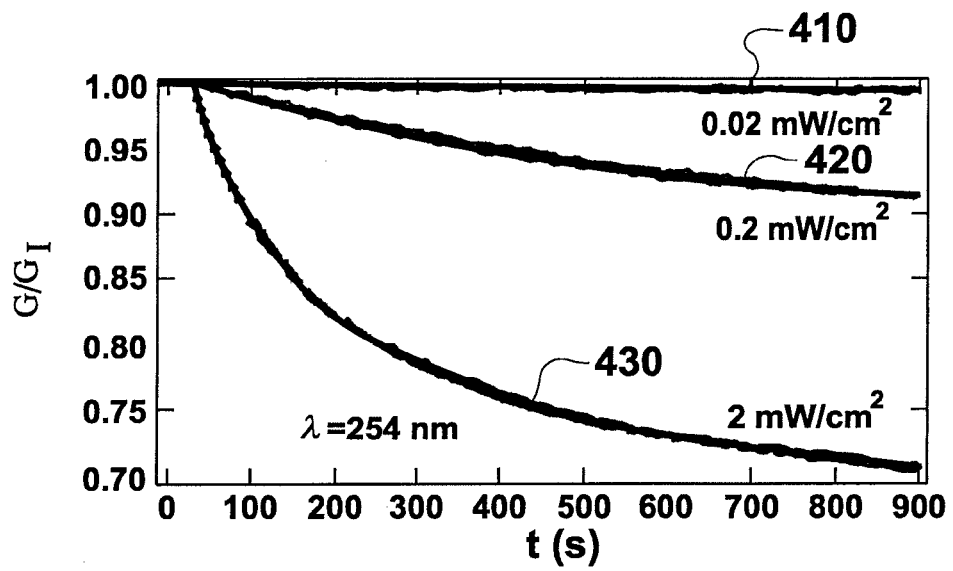
FIG. 4 is a graph showing conductance over time of a carbon nanotube undergoing photodesorption with different intensities of ultraviolet (UV) light, according to another example embodiment of the present invention.

In another example embodiment of the present invention, the intensity of UV light applied to a carbon nanotube is selected to achieve a desired conductance for implementation of the carbon nanotube in a particular circuit arrangement. FIG. 4 shows three specific implementations with different intensities, with curves 410, 420 and 430 each showing normalized conductance over time, as in the figures above, for UV light having a wavelength, $\lambda$, of about 254 nanometers with intensities of 0.02 $mW/cm^2$, 0.2 $mW/cm^2$ and 2.0 $mW/cm^2$, respectively. The light intensity may be varied, for example, using neutral density filters. In curve 410, the UV light intensity maintains the normalized conductance of the carbon nanotube at about 1.00. For a slightly lower conductance, the UV light intensity is applied as shown in curve 420, with the normalized conductance approaching about 0.90 at about 900 seconds of illumination. Finally, curve 430 shows UV illumination that achieves a normalized conductance that approaches about 0.70 at about 900 seconds of illumination. Each of these three implementations may be used, for example, for setting the conductance of the carbon nanotubes for implementation with a particular electronic circuit.

Figure 5:
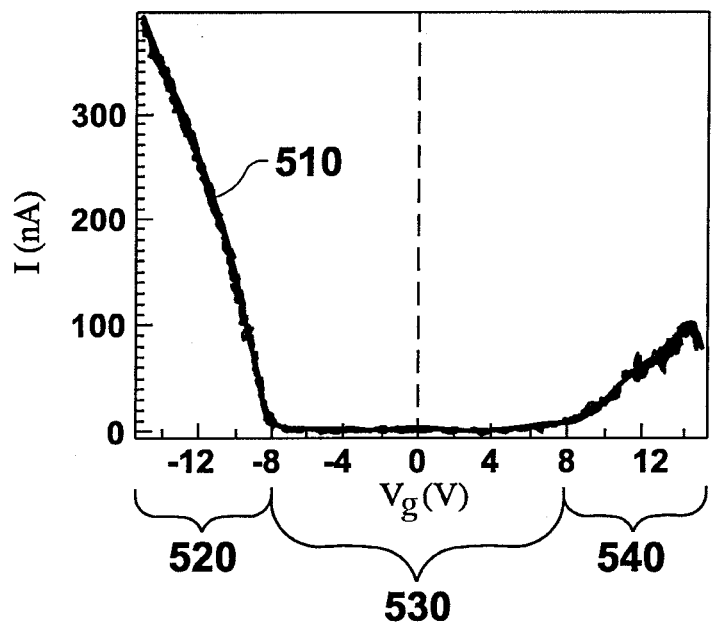
FIG. 5 is a graph showing current (I) versus gate voltage ($V_g$) of a carbon device undergoing photodesorption with ultraviolet (UV) light in a vacuum, according to another example embodiment of the present invention.

FIG. 5 shows a curve 510 with current (I, in nanoamps) versus gate voltage ($V_g$, in volts) for a circuit including a carbon nanotube over a substrate and a gate adapted to apply a gating voltage (e.g., via capacitive coupling) to the carbon nanotube, according to another particular example embodiment of the present invention. The carbon nanotube device is first placed in a vacuum chamber, and a vacuum is drawn on the chamber to about $1 \times 10^{-8}$ Torr. Light is directed to the carbon nanotube and desorbs molecules (e.g., $O_2$, $NH_3$, $NO_2$ and/or other molecules) therefrom. This photodesorption may, for instance, be carried out in a manner similar to the photodesorption discussed in connection with FIG. 3.

After the molecules are desorbed, the carbon nanotube device exhibits properties similar to an intrinsic semiconductor showing ambipolar FET behavior (e.g., both n-type and p-type FET behavior). More specifically, the device becomes insulating at $V_g$ of between about −8V and +8V, shown by curve portion 530, exhibits electrical transport through the valence band (e.g., p-type behavior) at curve portion 520 and exhibits electrical transport through the conduction band (e.g., n-type behavior) at curve portion 540. Therefore, the gate can be used to control the behavior of the circuit by applying voltages in the ranges shown.

Figure 6:
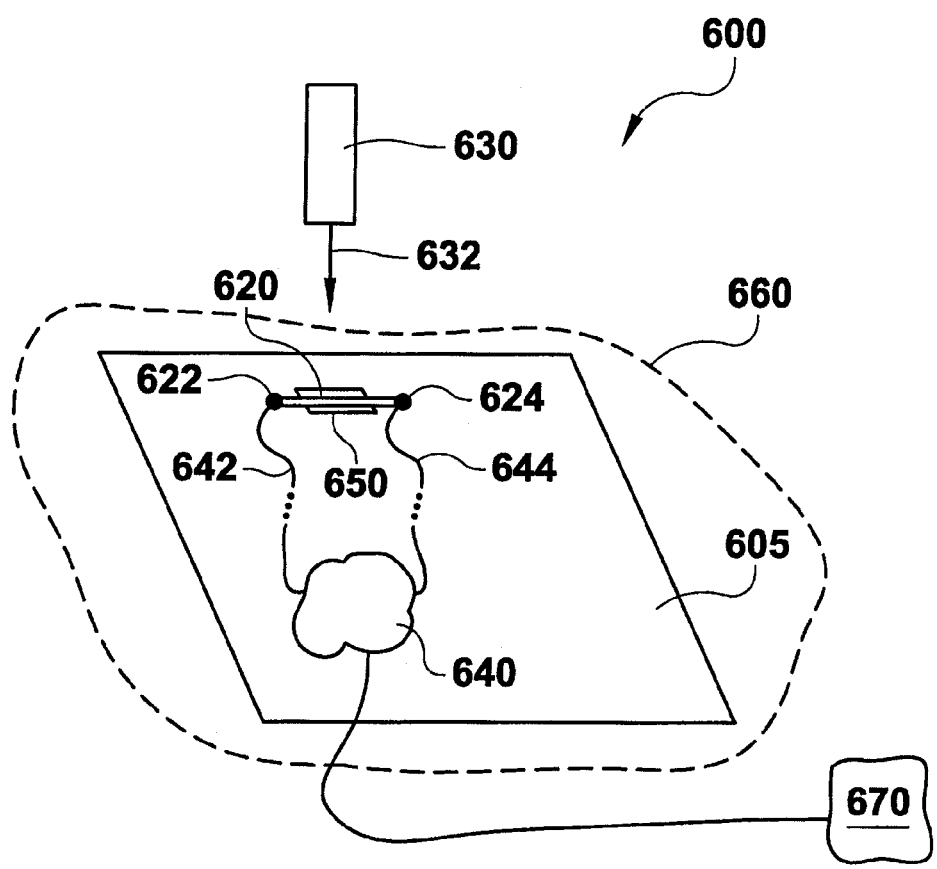
FIG. 6 is circuit arrangement including a carbon nanotube and a light source for molecular photodesorption from the carbon nanotube, according to another example embodiment of the present invention.

FIG. 6 shows a carbon nanotube circuit arrangement 600 using photodesorption for manipulating properties of a carbon nanotube, according to another example embodiment of the present invention. The circuit arrangement 600 includes a carbon nanotube 620, such as a SWNT, with opposite ends of the carbon nanotube 620 coupled to two electrodes 622 and 624. A light source 630 (e.g., an Ar ion diode laser, He—Ne diode laser and/or AlGaAs diode laser) is arranged over the substrate 605 for directing light 632 for desorbing molecules from the carbon nanotube 620. In one implementation, the light source 630 is part of the circuit arrangement 600 and activated, for example, using a control circuit also within the circuit arrangement 600. In another implementation, the light source 630 is separate from the circuit arrangement 600 and may be used, for example, during manufacture of the circuit arrangement 600.

The substrate 605 includes one or more commonly available semiconductor substrate materials, such as silicon and silicon-based materials. The electrodes 622 and 624 electrically couple the opposite ends of the carbon nanotube 620 to circuitry 640 in the device via interconnects 642 and 644. In one implementation, the electrodes 622 and 624 include a catalyst material, and in another implementation, the catalyst material is coated with conductive material. For general information regarding carbon nanotubes, and for specific examples of carbon nanotubes extending from catalyst particles that can be implemented in connection with the instant application, reference may be made to the above-referenced patent documents and publications.

The carbon nanotube 620 operates in the circuit arrangement 600 in a manner similar to that shown in the foregoing figures. Light 632 directed at the carbon nanotube 620 desorbs molecules therefrom, and the desorbed molecules are optionally removed from the circuit arrangement 600 (e.g., using a vacuum). The light 632 is controlled to manipulate properties, such as conductive behavior (including semiconductive behavior), of the carbon nanotube 620. For example, light can be directed at the carbon nanotube 620 for altering the conductance of the carbon nanotube as discussed in connection with FIGS. 2 and 3.

In another implementation, the circuit arrangement 600 further includes a gate 650 in the substrate 605. The gate 650 is arranged for applying a gating voltage to the carbon nanotube 620 for controlling the behavior of the carbon nanotube 620 in a manner similar to that discussed in connection with FIG. 5. Specifically, the carbon nanotube 620 exhibits p-type behavior under gating voltages below about −8V, exhibits insulative behavior at gating voltages of between about −8V and +8V and exhibits n-type behavior at gating voltages of over about +8V.

In another example embodiment of the present invention, the substrate 605 and the carbon nanotube 620 are enclosed in a chamber represented by dashed lines 660, with the chamber being adapted to draw a vacuum on the substrate 605. The light source 630 directs the light 632 into the chamber 660 and to the carbon nanotube 620, and a vacuum drawn on the chamber removes molecules desorbed from the carbon nanotube by the light 632. Alternatively, inert gas is filled in the chamber 660, which is particularly useful for preventing further adsorption of molecules to the carbon nanotube after they have been removed (e.g., due to the vacuum not removing all of the desorbed molecules from the chamber 660). The chamber 660 is then sealed and the light source 630 is removed. After the photodesorption, the carbon nanotube 620 exhibits properties similar to those shown in FIG. 5, and the sealed chamber 660 prevents additional molecules from contacting and adsorbing to the carbon nanotube 620. The gate 650 is adapted for applying voltages similar to those shown in FIG. 5, and the carbon nanotube 620 exhibits ambipolar FET behavior.

In one particular implementation, the light source 630 is separate from the circuit arrangement 600 and used during a manufacturing process of the device 600. Once the molecules are desorbed from the carbon nanotube 620, the chamber 660 discussed above is used to prevent further adsorption of molecules thereto and the carbon nanotube can be implemented in a circuit arrangement, where gas molecules are prevented from accessing the carbon nanotube 620. In one instance, the chamber 660 includes a semiconductor substrate in which the circuit arrangement 600 is buried. In another instance, the chamber 660 is a vacuum chamber used during manufacture of the circuit arrangement 600, which is subsequently buried in a semiconductor substrate that prevents molecules from adsorbing to the carbon nanotube 620.

In another implementation, the circuit arrangement 600 detects the wavelength of light 632 being applied thereto (e.g., as a photodetector). As discussed above, the carbon nanotube 620 responds differently to different wavelengths of light. In this regard, the circuitry 640 is used to detect the conductance of the carbon nanotube 620 across the electrodes 622 and 624. As the light 632 is directed to the carbon nanotube 620, the rate of change in conductance across the electrodes 622 and 624 is detected and used to identify the wavelength of the light, as discussed in connection with FIG. 1.

In another implementation, the circuit arrangement 600 is used for sensing molecular species. Molecules are exposed to the carbon nanotube 620 and adsorbed thereto. An electrical characteristic of the carbon nanotube 620 is detected via the circuitry 640 and electrodes 622 and 624. The electrical characteristic is used to identify the type of molecules adsorbed to the carbon nanotube 620, for example, using a change in resistance of the carbon nanotube to detect that a particular type of molecule has been adsorbed thereto. In one particular instance, the circuit arrangement 600 optionally includes a computer arrangement 670 coupled to the circuitry 640 and adapted for comparing the electrical response of the carbon nanotube 620 to known electrical responses of a carbon nanotube to a particular molecular species. When the response of the carbon nanotube 620 matches that of a known response, the molecules adsorbed to the carbon nanotube can be identified. After the molecules have been identified, the light source 630 directs light 632 to the carbon nanotube 620 to desorb the molecules therefrom, and the circuit arrangement 600 is ready for detecting another molecular species. With this approach, rapid desorption of molecules from the sensor is readily achieved, thus making possible rapid recovery of the sensor circuit arrangement 600 for use in detecting additional molecular species.

In still another implementation, the circuit arrangement 600 is implemented in a memory arrangement, with the carbon nanotube 620 being used to store data as a function of molecules adsorbed thereto. The light source 630 is configured and arranged to control the data by selectively desorbing molecules from the carbon nanotube 620. In one instance, the carbon nanotube 620 is exposed to an environment of a selected gas, such as $O_2$ and/or $NH_3$ and/or $NO_2$, molecules of which adsorb to the carbon nanotube 620. A first state of the carbon nanotube 620 involves the molecules being adsorbed to the carbon nanotube, which results in the carbon nanotube 620 exhibiting a first conductance. A second state of the carbon nanotube 620 involves the molecules not being adsorbed to the carbon nanotube (or a different amount of molecules being adsorbed to the carbon nanotube), as controlled by the light source 630, which results in the carbon nanotube exhibiting a second conductance. These first and second states of the carbon nanotube 620 are used as first and second memory states, such as "ON" and "OFF" states or "ONE" and "ZERO" states. The presence of the molecules is controlled via selective photodesorption from the carbon nanotube 620 with the light source 630, which switches the carbon nanotube 620 between states. With this approach, data can be written to and erased from the carbon nanotube 620, with the presence or absence of the molecules adsorbed to the carbon nanotube 620 effectively being the "data." The circuitry 640 is thus used to detect the state that the carbon nanotube 620 is in and to read out the state, such as for reading out a "ONE" or a "ZERO."

With the memory-arrangement approach discussed above in connection with FIG. 6, the carbon nanotube 620 may be implemented in a variety of memory applications. In one instance, the carbon nanotube 620 is replicated in an array of nanotube-memory cells (not shown) having molecules adsorbed thereto for read-only memory, with selective ones of the nanotube-memory cells being erased via photodesorption during a manufacturing process for the replicated carbon nanotubes. Alternatively, molecules are selectively adsorbed to the replicated carbon nanotubes, either in connection with or independently from the photodesorption.

In another particular implementation, photodesorption from carbon nanotubes is used to prevent reverse engineering of a circuit arrangement, such as the memory arrangement discussed above in connection with FIG. 6. For example, a carbon nanotube is erased in a vacuum and sealed in a circuit arrangement. When the nanotube is exposed to for reverse engineering, molecules such as Oxygen in air desorb onto the carbon nanotube, permanently altering the electrical characteristics of the circuit arrangement including the carbon nanotubes. Therefore, the state of conductance of the carbon nanotubes prior to exposure cannot necessarily be detected.

In another particular implementation, an array of carbon nanotubes is programmed by selectively adsorbing molecules to individual ones of the carbon nanotubes using, for example, the adsorption and photodesorption techniques discussed above. To deprogram the array, the carbon nanotubes are exposed to light to erase data (molecules) stored on the carbon nanotubes. This approach is particularly useful, for example, for one-time usage of data programmed onto the carbon nanotubes, as with a conventional read-only memory, such as EPROM.

In another instance, the circuit arrangement 600 is used as a fusible link for enabling or disabling an electrical connection, such as for enabling or disabling memory cells. By controlling the conductance of the carbon nanotube 620 via photodesorption of molecules adsorbed thereto, the carbon nanotube 620 can be used as a link, or switch, to close a circuit across the nodes 620 and 622. This fusible link is particularly useful for enabling or disabling circuitry, such as a particular memory bank or a particular circuit element. In addition, by making access to the carbon nanotube 620 difficult (e.g., by burying the carbon nanotube 620 in a semiconductor substrate), reverse engineering of the circuit in which the carbon nanotube is implemented is impeded due to the difficulty in detecting the conductance state of the carbon nanotube. For general information regarding fusible links, and for particular information regarding fusible links to which the present invention may be applied, reference may be made to U.S. Pat. No. 5,532,966 (Poteet, et al.), which is fully incorporated herein by reference.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include modifying the carbon nanotubes for sensing one or more particular molecular species, altering the circuit arrangements, and where appropriate, using the SWNTs as building blocks for more complex devices. Such modifications and changes do not depart from the true spirit and scope of the present invention. In addition, for general information regarding carbon nanotubes, and for specific information regarding carbon nanotube implementations that may be used in connection with the present invention, reference may be made to Appendices A and B, which form part of the underlying patent document and are fully incorporated herein by reference.

What is claimed is:

1. A method for using a carbon nanotube device including a carbon nanotube, the method comprising:
    using a light source to direct light at the carbon nanotube and to desorb molecules from the carbon nanotube;
    detecting a change in an electrical characteristic of the carbon nanotube; and
    using the detected change to detect that the molecules have been desorbed from the carbon nanotube.

2. The method of claim 1, wherein using a light source to direct light at the carbon nanotube includes exciting plasmons in the carbon nanotube with the directed light.

3. The method of claim 1, wherein using a light source to direct light at the carbon nanotube includes directing ultraviolet (UV) light at the carbon nanotube, the UV light having a wavelength that is sufficient to desorb the molecules from the carbon nanotube.

4. The method of claim 3, wherein directing UV light at the carbon nanotube includes directing UV light having a wavelength of about 254 nanometers.

5. The method of claim 4, wherein directing UV light at the carbon nanotube includes directing UV light having an intensity of about $2.0\ mW/cm^2$ at the carbon nanotube.

6. The method of claim 1, further comprising drawing a vacuum on the carbon nanotube and preventing molecules from adsorbing to the carbon nanotube, after using a light source to desorb molecules from the carbon nanotube.

7. The method of claim 1, further comprising:
    applying a voltage across the carbon nanotube before the step of detecting a change in an electrical characteristic of the carbon nanotube.

8. The method of claim 1, prior to using a light source to direct light at the carbon nanotube, further comprising:
    introducing molecules to the carbon nanotube;
    detecting an electrical characteristic of the carbon nanotube and detecting the presence of the molecules via the detected electrical characteristic; and
    wherein desorbing molecules from the carbon nanotube includes using the light source to purge the introduced molecules from the carbon nanotube.

9. The method of claim 1, further comprising sealing the carbon nanotube in a circuit arrangement that prevents molecules from adsorbing to the carbon nanotube, after using a light source to desorb molecules from the carbon nanotube.

10. A method for using a carbon nanotube device including a carbon nanotube, the method comprising:
    using a light source to direct light at the carbon nanotube and to desorb molecules from the carbon nanotube;
    drawing a vacuum on the carbon nanotube and preventing molecules from adsorbing to the carbon nanotube, after using a light source to desorb molecules from the carbon nanotube; and
    applying a gating voltage to the carbon nanotube.

11. The method of claim 10, wherein applying a gating voltage to the carbon nanotube includes applying the gating voltage such that the carbon nanotube exhibits electrical transport through the valence band in response to applying a high negative voltage thereto, exhibits insulative behavior in response to applying about zero voltage thereto and exhibits electrical transport through the conduction band in response to applying a high positive voltage thereto.

12. A molecular sensor comprising:
a carbon nanotube;
means for introducing molecules to the carbon nanotube, the molecules adsorbing to the carbon nanotube and changing an electrical characteristic thereof;
a detection circuit configured and arranged to detect the changed electrical characteristic of the carbon nanotube and to detect the presence of the adsorbed molecules via the changed electrical characteristic; and
a light source configured and arranged to direct light to the carbon nanotube, after detecting the presence of the adsorbed molecules, and to desorb the molecules from the carbon nanotube.

13. The molecular sensor of claim 12, wherein the detection circuit is further configured and arranged for detecting the composition of the molecules adsorbed to the carbon nanotube via the detected changed electrical characteristic.

14. A circuit arrangement comprising:
a carbon nanotube;
circuitry coupled across the carbon nanotube; and
a light source configured and arranged to direct light to the carbon nanotube for desorbing molecules therefrom.

15. The circuit arrangement of claim 14, wherein the light source is adapted to change the conductance of the carbon nanotube via the directed light.

16. The circuit arrangement of claim 14, further comprising:
a chamber that includes the carbon nanotube; and
a vacuum arrangement configured and arranged to draw a vacuum on the chamber.

17. The circuit arrangement of claim 16, wherein the vacuum arrangement is configured and arranged to remove desorbed molecules from the chamber.

18. The circuit arrangement of claim 14, further comprising a silicon substrate having a gate therein, the carbon nanotube being over the gate in the silicon substrate, the gate being configured and arranged to capacitively couple a voltage to the carbon nanotube.

19. The circuit arrangement of claim 18, wherein the carbon nanotube exhibits electrical transport through the valence band in response to the gate capacitively coupling a high negative voltage thereto, exhibits insulative behavior in response to the gate capacitively coupling about zero voltage thereto, and exhibits electrical transport through the conduction band in response to the gate capacitively coupling a high positive voltage thereto.

20. The circuit arrangement of claim 14, wherein the light source is configured and arranged to apply ultraviolet light to the carbon nanotube.

21. The circuit arrangement of claim 14, wherein the light source is configured and arranged to direct light having a wavelength of about 254 nanometers.

22. The circuit arrangement of claim 14, wherein the carbon nanotube exhibits a conductance that is a function of the wavelength of the light being directed thereto, and wherein the light source is configured and arranged to control the conductance of the carbon nanotube via the wavelength of the light directed thereto.

23. The circuit arrangement of claim 14, further comprising a gas supply configured and arranged to introduce a gas that attaches to the carbon nanotube and to increase the conductance of the carbon nanotube via the attached gas.

24. The circuit arrangement of claim 14, wherein the carbon nanotube exhibits a conductance that is a function of the intensity of the light being directed thereto, and wherein the light source is configured and arranged to control the conductance of the carbon nanotube via the intensity of the light.

25. A memory arrangement comprising:
a carbon nanotube;
a source configured and arranged to introduce molecules to the carbon nanotube for adsorbing the molecules to the carbon nanotube;
a light source configured and arranged to direct light at the carbon nanotube and to selectively desorb said molecules from the carbon nanotube;
memory circuitry electrically coupled to the carbon nanotube and configured and arranged for detecting an electrical characteristic of the carbon nanotube, the electrical characteristic being responsive to the molecules; and
wherein the detected electrical characteristic exhibits a first state in response to the carbon nanotube having the molecules adsorbed thereto and wherein the detected electrical characteristic exhibits a second state in response to the carbon nanotube not having the molecules adsorbed thereto.

26. The memory arrangement of claim 25, wherein the memory circuitry is configured and arranged for reading out a first value in response to the detected electrical characteristic exhibiting the first state and for reading out a second value in response to the detected electrical characteristic exhibiting the second state.

27. The memory arrangement of claim 25, wherein the light source is configured and arranged to selectively desorb the molecules in response to a write access to the carbon nanotube.

28. The memory arrangement of claim 27, wherein the light source is configured and arranged to switch the carbon nanotube between the first and second states, via the directed light, in response to signals applied to the light source.

* * * * *